(12) United States Patent
Fasoli et al.

(10) Patent No.: US 11,684,327 B2
(45) Date of Patent: Jun. 27, 2023

(54) PATIENT TABLE WITH LOCK AND UNLOCK DEVICE AND IMPROVED SAFETY ARRANGEMENTS

(71) Applicant: CEFLA Societá Cooperativa, Imola (IT)

(72) Inventors: Martino Fasoli, Imola (IT); Giulio Mattiuzzo, Imola (IT); Simone Chiampan, Imola (IT)

( * ) Notice: Subject to any disclaimer, the term of this patent is extended or adjusted under 35 U.S.C. 154(b) by 446 days.

(21) Appl. No.: 16/948,049

(22) Filed: Aug. 28, 2020

(65) Prior Publication Data
US 2021/0059619 A1    Mar. 4, 2021

(30) Foreign Application Priority Data

Sep. 2, 2019   (IT) .................. 102019000015333
Sep. 2, 2019   (IT) .................. 102019000015339

(51) Int. Cl.
*A61B 6/10*    (2006.01)
*A61B 6/04*    (2006.01)
*A61B 6/00*    (2006.01)
*A61B 5/00*    (2006.01)

(52) U.S. Cl.
CPC .............. *A61B 6/105* (2013.01); *A61B 5/704* (2013.01); *A61B 6/0407* (2013.01);
(Continued)

(58) Field of Classification Search
CPC ....... A61B 6/105; A61B 6/0487; A61B 5/704; A61B 6/0407; A61B 6/461; A61B 6/04;
(Continued)

(56) References Cited

U.S. PATENT DOCUMENTS 6,929,398 B1 *   8/2005   Tybinkowski ........... A61B 6/04
                                                          5/601
2005/0004444 A1   1/2005   Boninger
(Continued)

FOREIGN PATENT DOCUMENTS

CN       109966090 A  *  7/2019
DE       102016208328    8/2017
(Continued)

OTHER PUBLICATIONS https://www.vedantu.com/physics/white-light.*

*Primary Examiner* — David R Hare
*Assistant Examiner* — Deborah Talitha Gedeon
(74) *Attorney, Agent, or Firm* — Themis Law

(57) ABSTRACT

An imaging apparatus includes a patient table with a gurney and a base. The gurney can slide between two extreme positions, an electrically supplied motoreducer controlled by a control unit causing the table to slide and having a lock/unlock system of the sliding that is mechanical, independent from the electrical supply, and manually controlled by a grabbing organ actuated by a human operator. The patient table may be provided together with a gantry having a housing transparent to light for at least part of its extension, and a control unit of the radiographic apparatus. The housing or a part thereof is associated with a source of light, and the control unit, when the apparatus is electrically supplied, and/or other status conditions are determined by a status sensor, causes the light source to be illuminated and the housing to light up in its translucent parts signalling the status condition.

9 Claims, 8 Drawing Sheets

(52) U.S. Cl.
CPC ............ *A61B 6/0487* (2020.08); *A61B 6/461* (2013.01); *A61B 6/04* (2013.01); *A61B 6/0442* (2013.01); *A61B 6/0471* (2013.01); *A61B 6/102* (2013.01); *A61B 6/107* (2013.01)

(58) Field of Classification Search
CPC ..... A61B 6/0442; A61B 6/0471; A61B 6/102; A61B 6/10; A61B 6/107; A61B 6/42; A61B 6/4266; A61B 6/00; A61N 2005/0626; A61N 2005/0629; A61N 2005/0658; A61N 2005/0663; A61N 2005/1063; A61N 5/1049; A61N 5/1048; A61N 5/1064; A61G 2210/50; A61G 13/02; A61G 2203/10; A61G 2203/30; A61G 13/0018; A61G 13/104; A61G 2203/40; A61G 7/018; Y10S 5/943
See application file for complete search history.

(56) References Cited

U.S. PATENT DOCUMENTS

| | | |
|---|---|---|
| 2006/0058601 A1 | 3/2006 | Smith |
| 2009/0080186 A1 | 3/2009 | Helmreich |
| 2011/0082348 A1* | 4/2011 | Herold .................. A61B 6/037 |
| | | 600/249 |
| 2014/0266204 A1 | 9/2014 | Watanabe |
| 2015/0272518 A1 | 10/2015 | Koerth |
| 2017/0156684 A1 | 6/2017 | Van de Rijdt |

FOREIGN PATENT DOCUMENTS

| | | |
|---|---|---|
| EP | 0923922 | 6/1999 |
| EP | 3061496 | 8/2016 |
| JP | 2015066125 | 4/2015 |
| WO | 2018006858 | 12/2018 |

* cited by examiner

PATIENT TABLE WITH LOCK AND UNLOCK DEVICE AND IMPROVED SAFETY ARRANGEMENTS

FIELD OF THE INVENTION

The present invention relates to an extraoral radiographic apparatus for the acquisition of volumetric three-dimensional images. In particular, the invention relates to a safety lock/unlock system of the table's gurney on which the patient is lying in order to acquire radiographic images.

The present invention finds advantageous, but not exclusive, applications in computerized tomography scanners used in dentistry, to which the ensuing description will make explicit reference, without implying any loss of generality. The present invention may also be advantageously applied to other imaging apparatuses that include a patient table and a gantry, but based on a different physical principle, like Magnetic Resonance Imaging (MRI) or Position Emission Tomography (PET), etc.

BACKGROUND OF THE INVENTION

Computerized tomography scanners having a gantry supporting a lying patient, used in dental practice and hospitals, generally include a frame supporting a gurney for a lying patient, and an X-ray source-detector assembly. Said assembly is designed to rotate about an anatomical area of analysis for acquiring raw volumetric tomographic data of an anatomical area of interest of the patient, such as. head, limbs, or portions of the vertebral column.

Preferably, but not necessarily, the radiographic technology is cone-beam volumetric radiography (also known as CBCT or 3D), i.e. the acquisition from different projection angles, of a series of two-dimensional radiographic images, which are processed post-acquisition to reconstruct three-dimensional volumes.

The tomography scanner further comprises a control unit, connected to the source-detector assembly, for controlling emission and reception of the beam in a way synchronous with the rotation of the arm, and a processing unit connected to the detector for receiving, storing, and processing the volumetric tomographic data so as to reconstruct images of the object. The processing unit is provided with a screen to enable the visualization of the reconstructed images.

As mentioned, the apparatus typically comprises a table on which a patient lies to acquire images, and a gantry hosting the X-ray source-detector (or sensor) assembly. The patient table is provided with a gurney which can slide inside and outside the gantry, so as to acquire different anatomical areas of a patient. Typically, the patient lies down on the table gurney while the gurney is in its extracted position in relation to the gantry. After this, the gurney is raised/lowered or laterally displaced so as to bring it in correspondence to the gantry hole, and then the gurney is slid inside the gantry up to a position suitable for acquiring the specific radiographic image; then the image acquisition can start. The acquisition takes place while the X-ray source and detector rotate around the patient. Once the acquisition is completed, the gurney is extracted from the gantry and the patient can stand up for releasing.

Therefore, the table gurney is substantially provided with two extreme positions:

An extracted position with respect to the gantry, allowing the patient to access the gurney or to leave the gurney;

An inserted position in the gantry, up to the end of excursion.

The intermediate positions between the extracted positions and the completely inserted position allow to acquire a wide range of anatomical areas (head, limbs, portions of vertebral column).

Obviously, it is fundamental that the gurney is stable when it is in its inserted position, during which image acquisition occurs, as any displacement might lead to movement artefacts, and therefore to the need of repeating the acquisition, with the ensuing administration of a useless and damaging X-ray dose to the patient. Therefore, when the gurney is inserted in the gantry, it is blocked so that it cannot be moved until the end of the acquisition.

Nonetheless, an emergency might occur, and therefore there might be the need to rapidly extract the gurney from the gantry: e.g. in case of a sudden illness of the patient, blackout or other, preventing the trapping of the patient.

U.S. Pat. Nos. 7,028,356B2 and 7,621,007B2 to GE Medical Systems disclose a braking system for the rotation axis for a patient positioning device.

U.S. Pat. No. 6,651,279 again to GE Medical Systems discloses a system and a method to prevent the collision in a patient positioning system.

EP923922 to Stille Beta Inc. discloses an operatory table for both surgical procedures and digital imaging. It is provided with two blocks, one for preventing longitudinal movements, and the other for preventing lateral movements.

WO2018226858 to EPICA Int. discloses a radiographic table for an easier access to a region of interest of a patient.

Typically, any radiographic equipment is provided with a panic button, which can be pressed by a human operator or by anyone in case of necessity, having the aim of interrupting the working of the radiographic apparatus by stopping its electrical supply.

A drawback of the known art is that patient table and gantry are integral, but the table moves with respect to the gantry. For ergonomics reasons, lowering the table with extracted gurney is preferable, so as to facilitate the access of patients. Nonetheless, in its access positions, frequently the table gurney is in a position lower than the gantry hole, and if the gurney is pressed against the gantry there might be an accidental collision with ensuing damages to the gantry itself. Therefore, there are provided anti-collision elements in order to prevent these risky situations. It is worth noting that the anti-collision safety must be warranted in any condition, even in the absence of electrical supply or with switched-off apparatus. This can be in contrast with the need of extracting the patient even in case of blackout, or activation of the panic button stopping the electrical supply, when the patient is under an acquisition inside the gantry.

It is known that X-rays are ionizing radiations that cause damage to living tissue, and can cause mutations, acute radiation syndrome, cancer and death.

X-rays are invisible and not directly detectable by human senses.

In the art, it is known to place on the door of X-ray rooms a device that lights up and/or emits an acoustic signal when the radiographic apparatus is emitting X-rays.

Moreover, there are provided standards that prescribe to provide the radiographic apparatuses with light or acoustic signals that are activated in correspondence of X-rays emission.

Particularly, in combination with the above mentioned emergency situations in which there might be the need to rapidly extract the gurney from the gantry: e.g. in case of a sudden illness of the patient, blackout or other, preventing the trapping of the patient, the doctors or the service persons might need to act rapidly and enter the room where the apparatus is placed. Due to hurry for intervening rapidly on the patient, there might occur that the safety indications are disregarded or not noticed. Furthermore, the current light signals indicating that the apparatus is in use and that radiation is emitted by the sources are indirectly related to the functional status of the apparatus itself, in the sense that if a failure of the system occurs in the feedback signal to the system controlling the light signals at the door of the room, the apparatus might still be operating although the light signal placed at the door of the room is indicating that the apparatus is not operative.

Possible solutions could be to provide a vital safety system controlling the light source driver and which vital safety system disactivates the power supply to the apparatus or at least the power supply to the radiation source in case of a failure of the driver controlling the light source and/or the light source itself. Such systems are known in other technology fields and, although their function could solve the problem, the vital safety systems of this kind are complex and expensive. As a result, no measure is taken to enhance the security of the signaling units associated to the functional status of the scanning apparatus.

SUMMARY OF THE INVENTION

A first aim of the present invention is providing a radiographic apparatus with lying patient allowing to extract the table gurney from the gantry in a fast and efficient way, and to block it in the desired position in a likewise fast and efficient way.

This object is achieved by an apparatus and a method having the features disclosed hereinafter. Advantageous embodiment and refinements are also described hereinafter.

In particular, the present invention relates to an insertion system operable with a lock/unlock system of the table gurney, allowing to extract the table gurney from the gantry, and to block it inside the gantry in a fast and efficient way, connecting/disconnecting it to an automatic movement system.

The lock/unlock system according to the present invention is capable of blocking the gurney in the two said extreme positions and in all its intermediate positions.

According to the present invention, the extraction stroke or excursion of the gurney with respect to the gantry is in the order of 150 cm; the extracted position allows the patient to exit from the gantry without difficulties.

In particular, the lock/unlock system according to the present invention disengages, through an handle, a driving pulley, working as a purely mechanical insertion, while a sensor sends a signal to the control unit in order to warn that the gurney is in a state of insertion or dis-insertion for the anti-collision with the apparatus.

The safety lock/unlock system is provided with important advantages.

A first advantage of the table provided with lock/unlock system according to the present invention consists in the possibility of manually moving the table gurney even in the absence of electrical supply.

A second advantage lies in providing the human operator with the possibility of accelerating the operation of insertion/extraction of the patient by manually acting on the table gurney, blocking it in the position needed for acquiring the specific radiographic acquisition, while bypassing some automatic positioning procedures, which may require a longer time.

A third advantage consists in the fact that the lock/unlock operation in case of emergency is intuitive and fast, as it requires to act on the only handle present on the apparatus.

In combination with the above first aim, the invention has a further aim consisting in providing the above safety functions in relation to the manual locking and unlocking of the patient table in combination with a reliable system allowing to signal in a safe way the operative condition of the apparatus, and particularly of the radiation source, so that the signal can be seen in a very easy and direct way and allow the service persons to take measures for acting very rapidly and switching the apparatus in a secure status, particularly, but not exclusively, in relation to the operative condition of the radiation source.

This object is achieved by an apparatus and a method having a gantry with frontal housings having big dimensions, made of translucent or opaline plastic materials, capable to allow an effect of retro-illumination that allows to visually detect the emission of X-rays in a very efficient way.

According to an embodiment, a radiographic apparatus is disclosed comprising a gantry (3) in its turn comprising a housing (6) transparent to light radiations for at least part of its surface extension, and a control unit of the radiographic apparatus (1), wherein the radiographic apparatus further comprises a carter to which at least a source of monochromatic or polychromatic light radiation is associated, and said control unit is configured so as to allow that, when said apparatus or at least a radiation source is electrically supplied, i.e. active, said light radiation source is illuminated and said housing (6) lights up in its translucent parts.

Advantageous embodiment and refinements are specified hereinafter.

A preferred embodiment provides for different lighting effects, or the emission of light having different colors according to the status of the radiographic apparatus.

A further preferred embodiment provides, in combination with the above, that at least one light effect is uniquely related to the condition in which the radiation source is active and a further different light effect, such a specific color or a particular blinking sequence of only one or more colors is related to the condition of the lock/unlock system of the table gurney and/or a further light effect such a specific color or a particular blinking sequence of only one or more colors is related to an emergency condition requesting to carry out manual lock or unlock of the gurney.

According to a variant embodiment the translucent carter may be provided with more than one light source distributed at different zones of its surface, the light sources being activatable independently in one form the other in order to provide for different light effects.

The zones may be also separated by delimitation lines, which are visible and traced on the outer surface of the carter.

According to a particular embodiment, three zones are at least provided at the upper half of the carter, one for signaling the condition of the radiation source or of the apparatus, one for signaling the emergency request and the third for signaling the status of the lock/unlock system.

A first advantage of the present invention is modulating the color of the emitted light using LEDs of different colors as light source, according to the desired effect. E.g., green light might mean "ready for acquisition", red light signal that an error occurred, yellow light that X-ray emission is under way, etc.

A second advantage is conferring to the radiographic apparatus a diffused lighting effect that contributes to patient's relaxation during the acquisition of radiographic images, so as to facilitate patient's immobility.

It is worth noting that keeping the patient under radiographic acquisition in a tranquil state wherein she/he can maintain the immobility required for the whole duration of the acquisition is very important. As a matter of fact, both the reduced dimensions of the gantry hole, and the noises emitted by the gantry during the acquisition may induce stress in patients, up to triggering claustrophobia attacks in more phobic patients.

BRIEF DESCRIPTION OF THE DRAWINGS

Additional advantages and properties of the present invention are disclosed in the following description, in which exemplary embodiments of the present invention are explained in detail based on the drawings.

DETAILED DESCRIPTION OF EMBODIMENTS OF THE INVENTION

Figure 1:
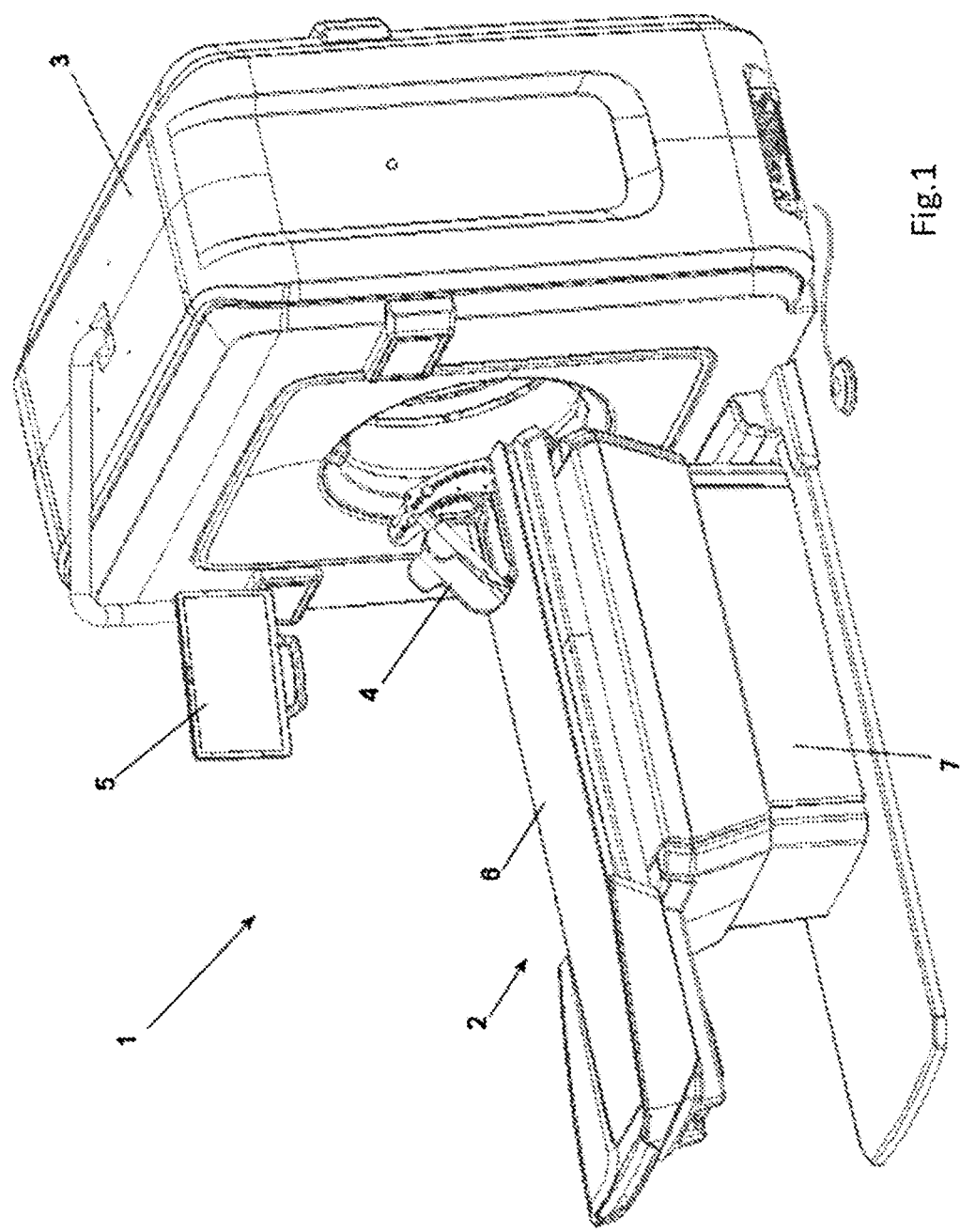
FIG. 1 is an axonometric view of the radiographic apparatus according to the present invention, with the gurney in its extracted position (first extreme position)

FIG. 1 shows an extraoral radiographic apparatus 1, comprising a table 2 for positioning a patient (not shown) in a lying position, and a gantry 3, in its turn comprising a X-ray source and detector (not shown).

The table 2 comprises a base 7 resting on the floor and integral with gantry 3, and a gurney 6, mobile with respect to the base. The patient rests on said gurney 6. Optionally, there is provided an adjustable device 4 for immobilizing patient's head, which is fixed to said gurney 6.

Said gantry 3 comprises a screen 5 to visualize the patient's images or an instruction panel.

Figure 2:
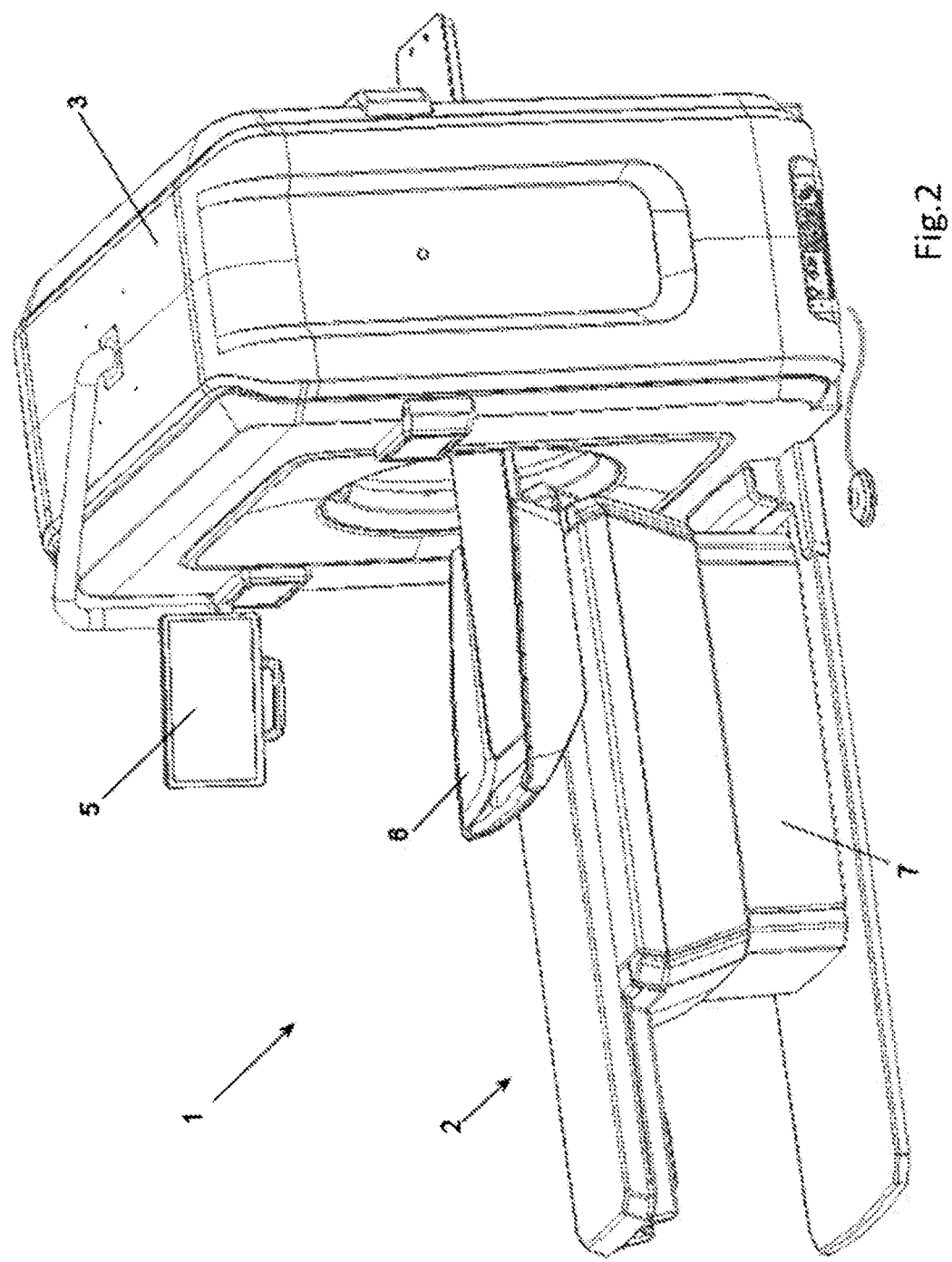
FIG. 2 is an axonometric view of the radiographic apparatus according to the present invention, with the gurney in its end of stroke inserted position (second extreme position)

FIG. 2 shows the same elements shown in FIG. 1.

In the two figures, the gurney 6 is shown in its two extreme positions: in FIG. 1 the gurney 6 is shown in its completely extracted position, while in FIG. 2 the gurney 6 is shown in its position inserted in the gantry 3 up to its end of stroke.

The lock/unlock system according to the present invention enables the fast and safe lock/unlock of the gurney 6 with respect to its base 7, allowing the gurney 6 to be locked in one of the two extreme position shown in the FIGS. 1 and 2, and in all the intermediate positions therebetween.

Figure 3:
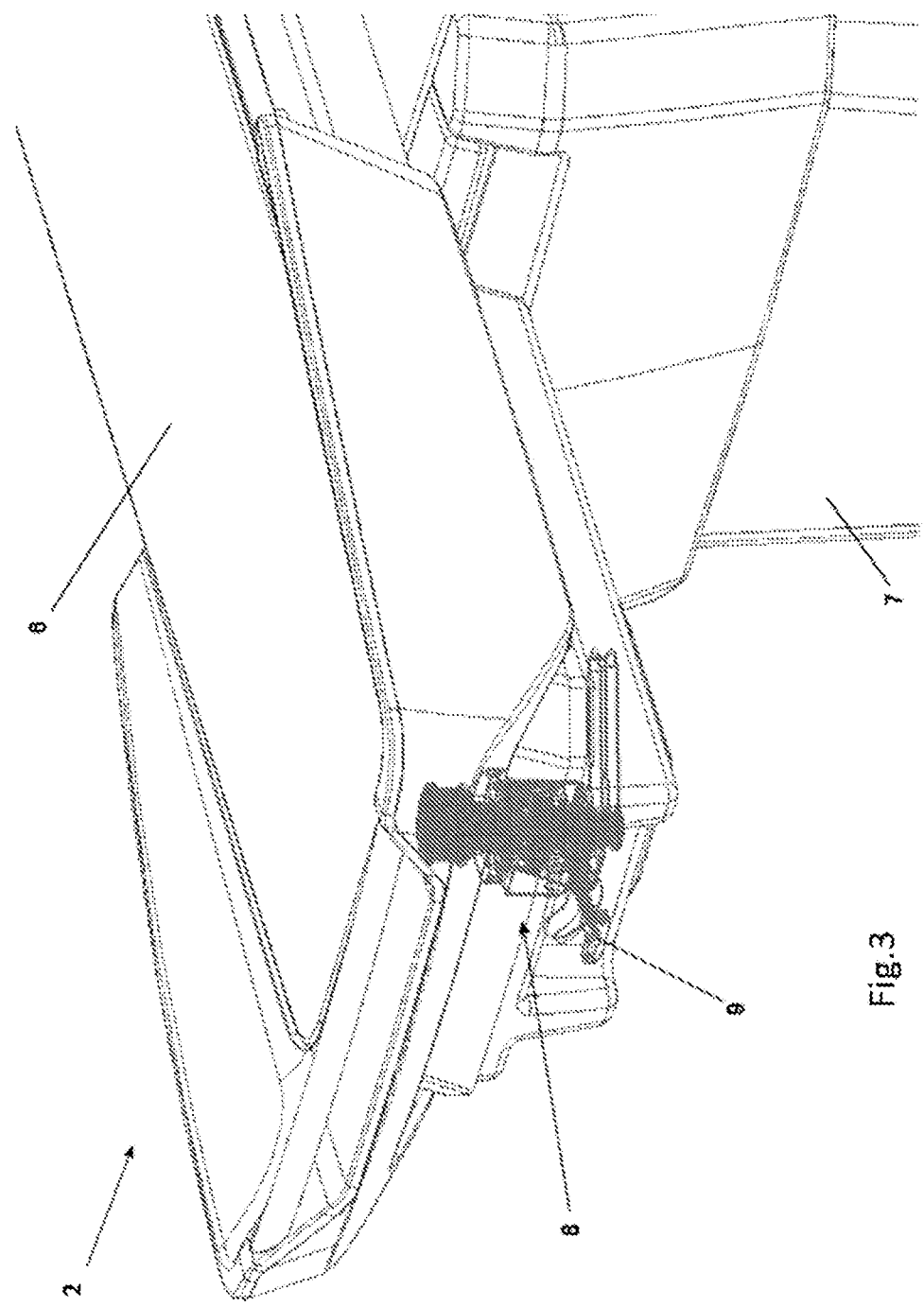
FIG. 3 is a detail of the table with transparent housings in order to show the position of the lock/unlock system according to the present invention, axonometric view.

FIG. 3 shows a detail of the patient table 2 provided with the lock/unlock system 8 according to the present invention. The housings have been made transparent in order to show the position of the lock/unlock system 8 inside said table 2.

Figure 4:
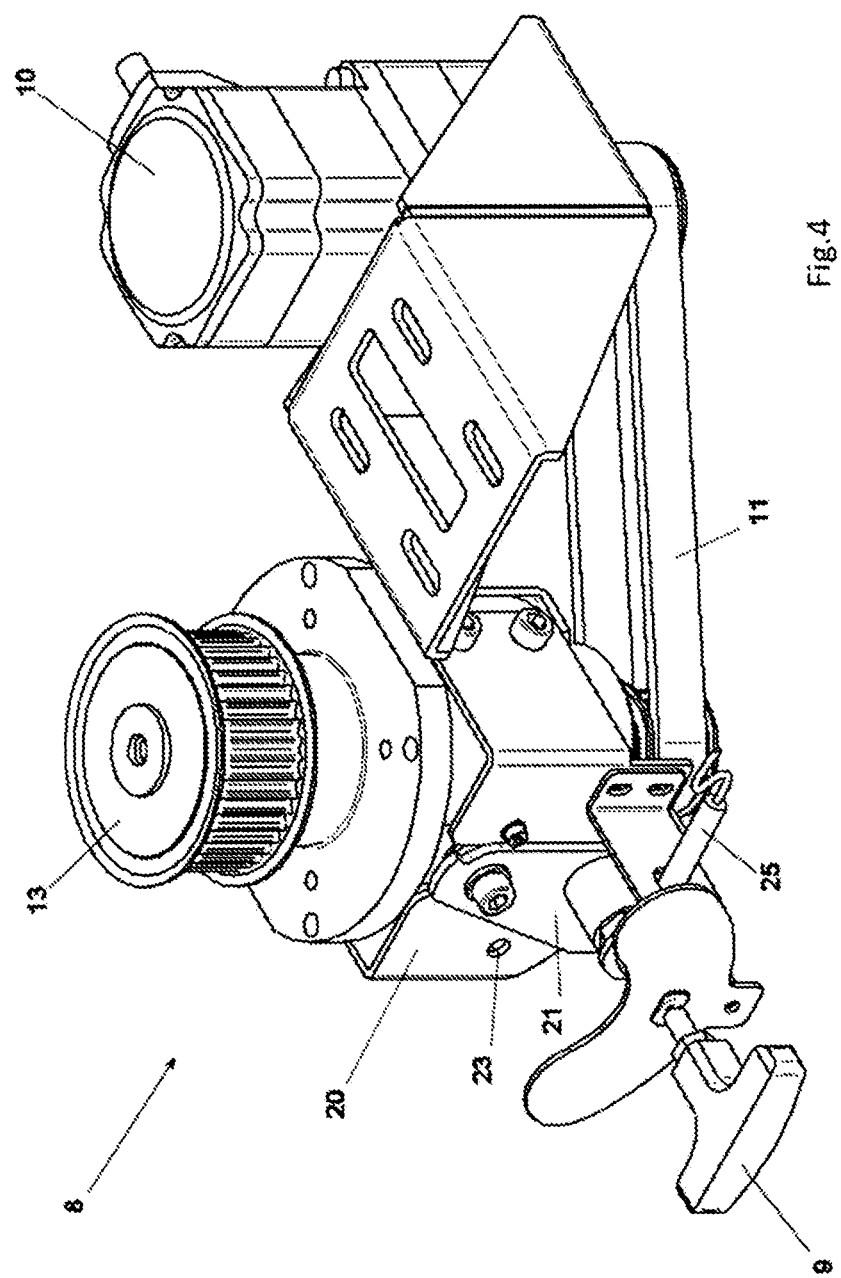
FIG. 4 is an axonometric view of the lock/unlock system.

From the distal end of the patient table 2, under the gurney 6, a handle 9 protrudes, allowing a human operator to manually act on the lock/unlock system 8. FIG. 4 shows an axonometric view of the lock/unlock system 8.

The lock/unlock system 8 is provided with said handle 9, a moto-reducer 10 actuating a drive belt 11, which in its turn engages a pulley 12 (visible in FIG. 5), which actuates all the mechanism of the insertion, transferring or disconnecting the motion which is transmitted to a further pulley 13. Said pulley 13 actuates the forward/backward movement of the gurney 6 through a (not shown) belt. Said moto-reducer 10 is controlled by the (not shown) control unit of the apparatus 1.

The handle 9 can take two extreme positions: a lock position, wherein the movement of the moto-reducer 10 is transmitted, and an unlock position, wherein the movement of the moto-reducer 10 is idle.

Figure 5:
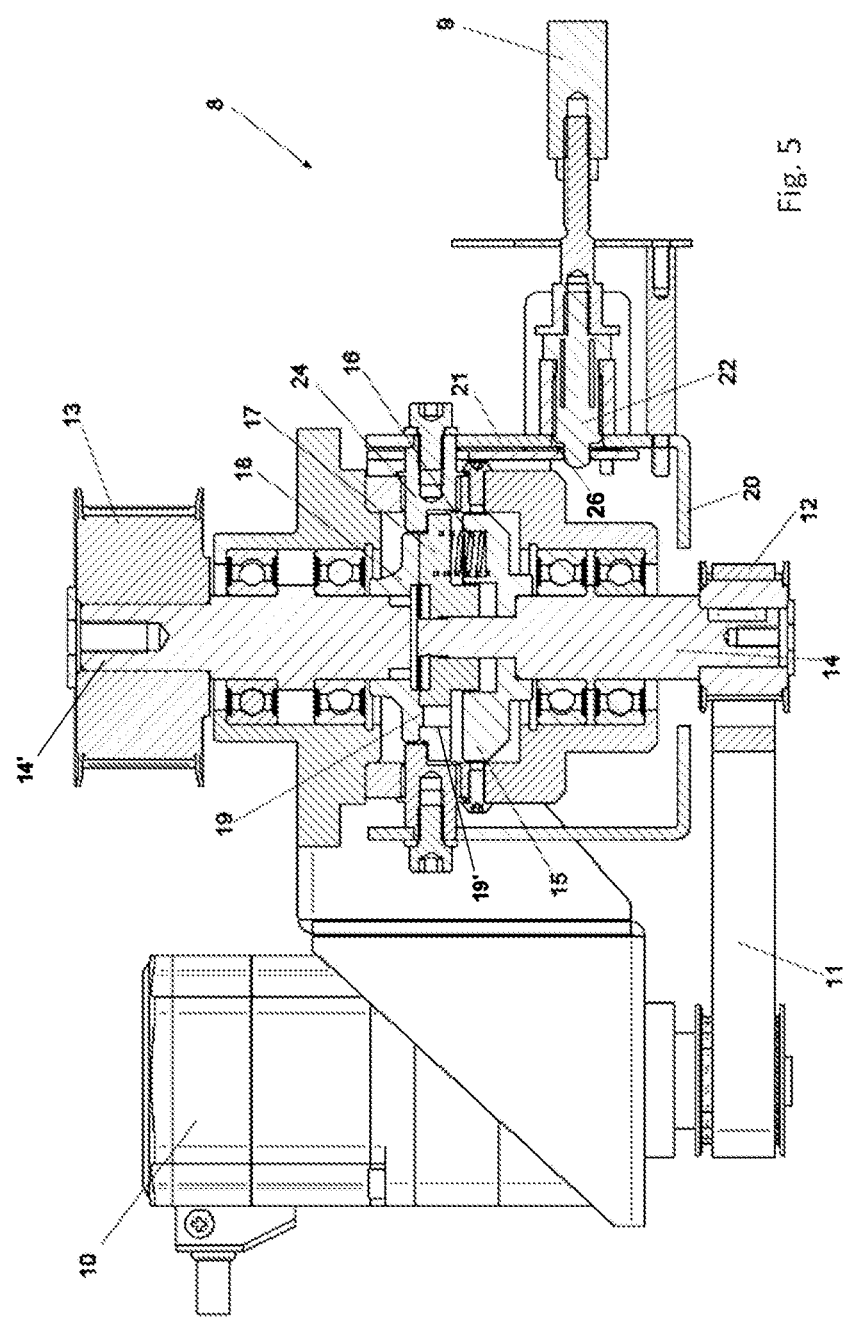
FIG. 5 is a section of the lock/unlock system.

FIG. 5 shows a section of the lock/unlock system 8, wherein all the above-quoted elements are shown, with other elements which are visible only in section.

The section shows the configuration of the system in the inserted condition, wherein the lock/unlock system 8 transmits the movement of the moto-reducer 10 to the gurney 6.

The drive belt 11 actuated by the moto-reducer 10 moves the pulley 12 mounted on a shaft 14. On the shaft 14 there is fixed a plate 15 that rotates integrally with said shaft 14. Said plate 15 is the seat wherein a plurality of springs 16 are positioned. Said springs 16 work in compression on a disk 17, in its turn integral with the shaft 14, which is the female portion of the mechanical insertion. The disk 17 is free to axially slide on the shaft 14, when the springs 16 are compressed. The disk 17 is provided with a plurality of holes 19' operating as insertion seats in which small pins 19 engage, which are an integral part of a second disk 18, which is the male portion of the mechanical insertion and which is mounted on shaft 14'.

When the human operator wants to manually intervene on the extraction of the patient from the gantry, she/he acts on the lock/unlock system 8 through the handle 9, de-coupling the movement of the moto-reducer 10 from the movement of the gurney 6.

The lock/unlock system 8 is provided with two brackets, a first fixed bracket 20 and a second mobile bracket 21, which can rotate for about 40°, on which said handle 9 is mounted. The handle 9 can perform a roto-translation movement, with a linear component represented by the extraction of the handle towards the human operator, and a rotatory component integral to said mobile bracket 21.

To the end opposed to the one grabbed by the human operator, said handle 9 is provided with a spring pin 22, which in the condition of insertion engages a hole 26 of insertion on said bracket 20, blocking the system in a position wherein the movement of the moto-reducer 10 is transmitted.

When the human operator pulls the handle 9 toward her/himself, i.e. toward the outside of the table, she/he extracts the spring pin 22 from the insertion hole 26, and this allows to rotate said handle of about 40°, and therefore the mobile bracket 21, so finding a second end position, which entails a dis-insertion hole 23 (visible in FIG. 4), wherein the spring pin 22 can be inserted for release of the handle 9.

The mobile bracket 21 is swiveled on an eccentric pin 24, which rotating for about 40° between two said extreme positions insists on the female disk 17, pushing it axially up to detaching the insertion made of the holes provided on it and of the small pins 19 of the male disk 17. In this way, the female disk 17 compresses the springs 16.

When the handle 9 goes back to its inserted position, the springs 16 bring back the disks 17 and 18 in their block position, wherein the moto-reducer 10 resumes the transmission of motion.

Near the handle 9 and integral to the mobile bracket 21 there is provided a proximity sensor 25 (visible in FIG. 4), which recognizes the axial position of the handle 9 and therefore of the spring pin 22. When the spring pin 22 is inserted in the insertion hole 26, the proximity sensor 25 is active, and communicates to the (not shown) control unit of the apparatus 1 that the gurney is automatically moved. As the position of the gurney 6 is known, through a position feed-back the apparatus 1 can safely operate, without the risk of collision with the gantry 3.

On the other hand, when the handle 9 is pulled, even without rotating it, the sensor 25 does not detect any contrast element, and communicates to said control unit of the radiographic apparatus 1 that the transmission of motion from the moto-reducer 10 is de-coupled, therefore the gurney 6 can be manually moved in any position between its two extreme positions. In this condition, which does not warrant the certainty of anti-collision, e.g. in absence of electrical supply of the apparatus 1, or by activation of the panic button, the control unit inhibits some of the automatic movement functions of the table (e.g. the vertical movement of the table), so as to prevent that the human operator can move the table causing an accidental collision with the gantry 3.

In an embodiment, when the handle 9 is pulled, the control unit inhibits the emission of X-rays.

According to the further features provided in combination with the lock/unlock system for improving the safety performances of the apparatus, said gantry 3 comprises a hole 107 (better visible in FIG. 6) allowing the entrance of the table gurney 6 which supports the patient, and a translucent housing 60 allowing the passage of light, placed behind said housing. Both elements are better visible in FIG. 6.

The housing is realized partially translucent and partially opaque in one or more areas of said housing, which areas can also be distanced from each other, and realized according to a pre-set design.

Figure 6:
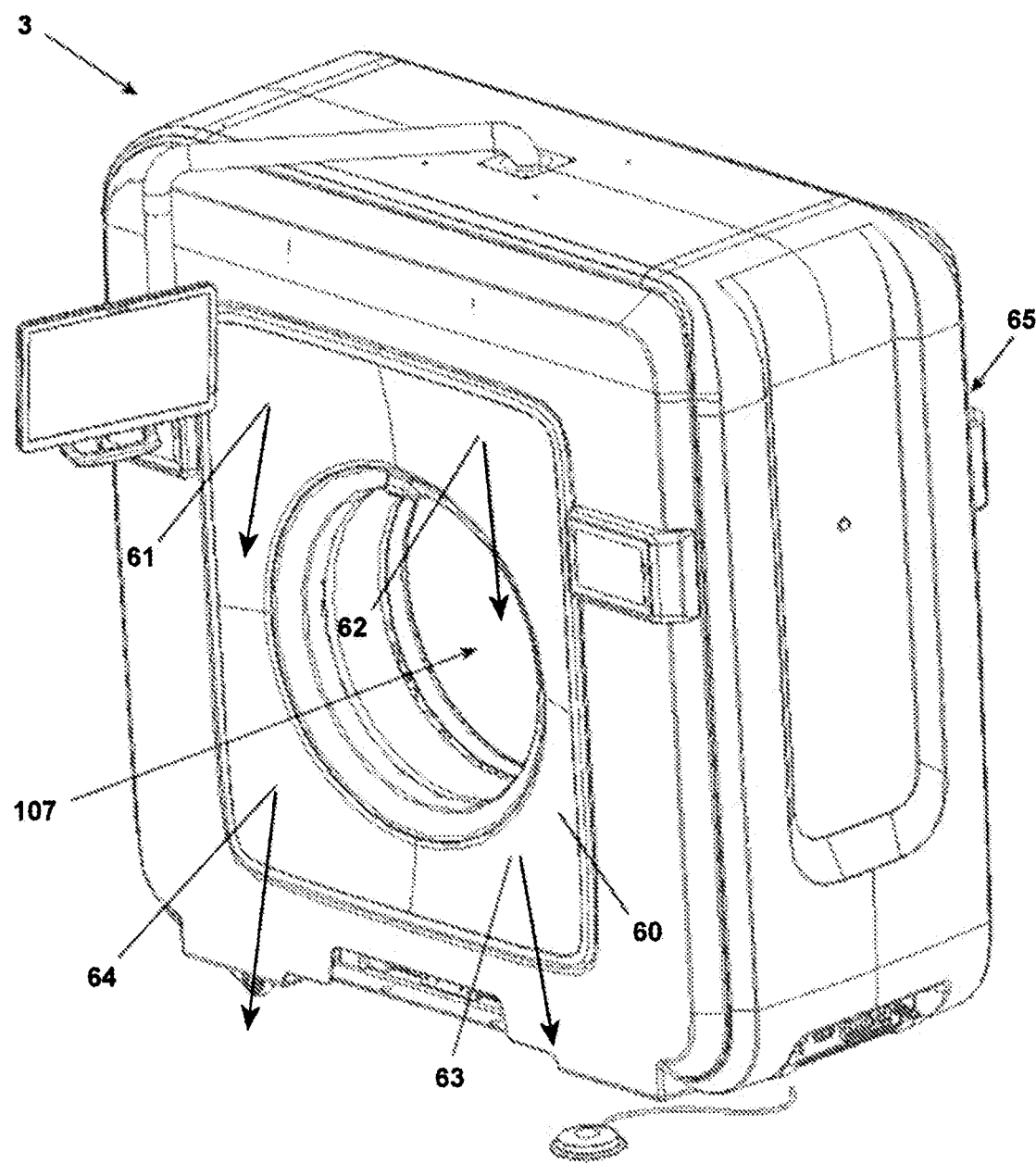
FIG. 6 is an axonometric view of a switched-on radiographic apparatus according to the present invention, detail of the gantry.

FIG. 6 shows four areas 61, 62, 63, 64.

Therefore, it is apparent that at least a part of the wall forming the housing or the case of the gantry is realized in a translucent material, or alternatively at least part of the wall of said housing carries at least a panel of translucent material on its outside.

FIG. 6 shows said gantry 3 only, with a lightened translucent housing 60. The light rays are represented as arrows that come out from the housing 60.

Figure 7:
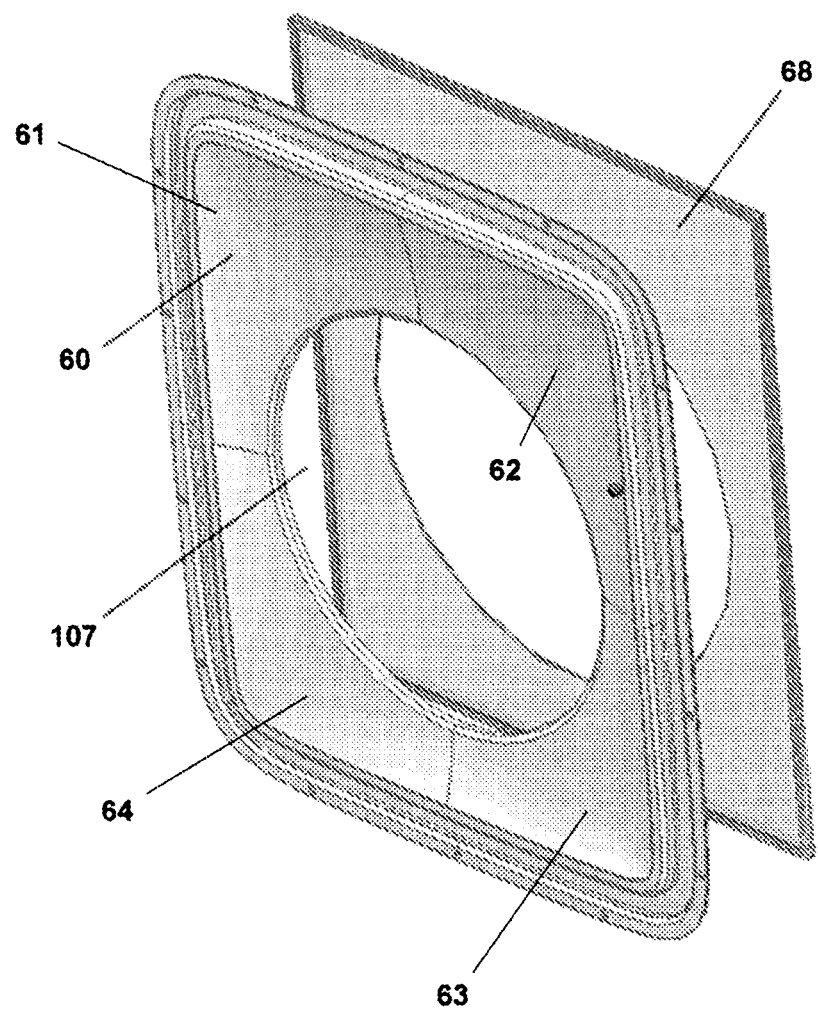
FIG. 7 is an exploded view showing a translucent housing and a diffusor panel, in an axonometric view.

FIG. 7 shows an exploded view comprising said translucent housing 60 and a light diffusor panel 68 placed inside said gantry 3, therefore behind to said housing 60 for an observer looking at the gantry from outside.

Said diffusor panel 68 is provided with a known structure, comprising a sandwich of plastic elements having the function of diffusing in a uniform and monodirectional way the light emitted by at least a LED strip placed on a side of said panel 68.

As it is apparent from Figures, according to a non-limiting embodiment, the translucent wall is adjacent to the entrance hole of said gantry.

The specific form shown just as an example shows an element of translucent material which completely surrounds said entrance hole 107 of the gantry, extending for a given radial length even on the surface of the housing on the head side of the housing associated with the entry side of the gantry.

Figure 8:
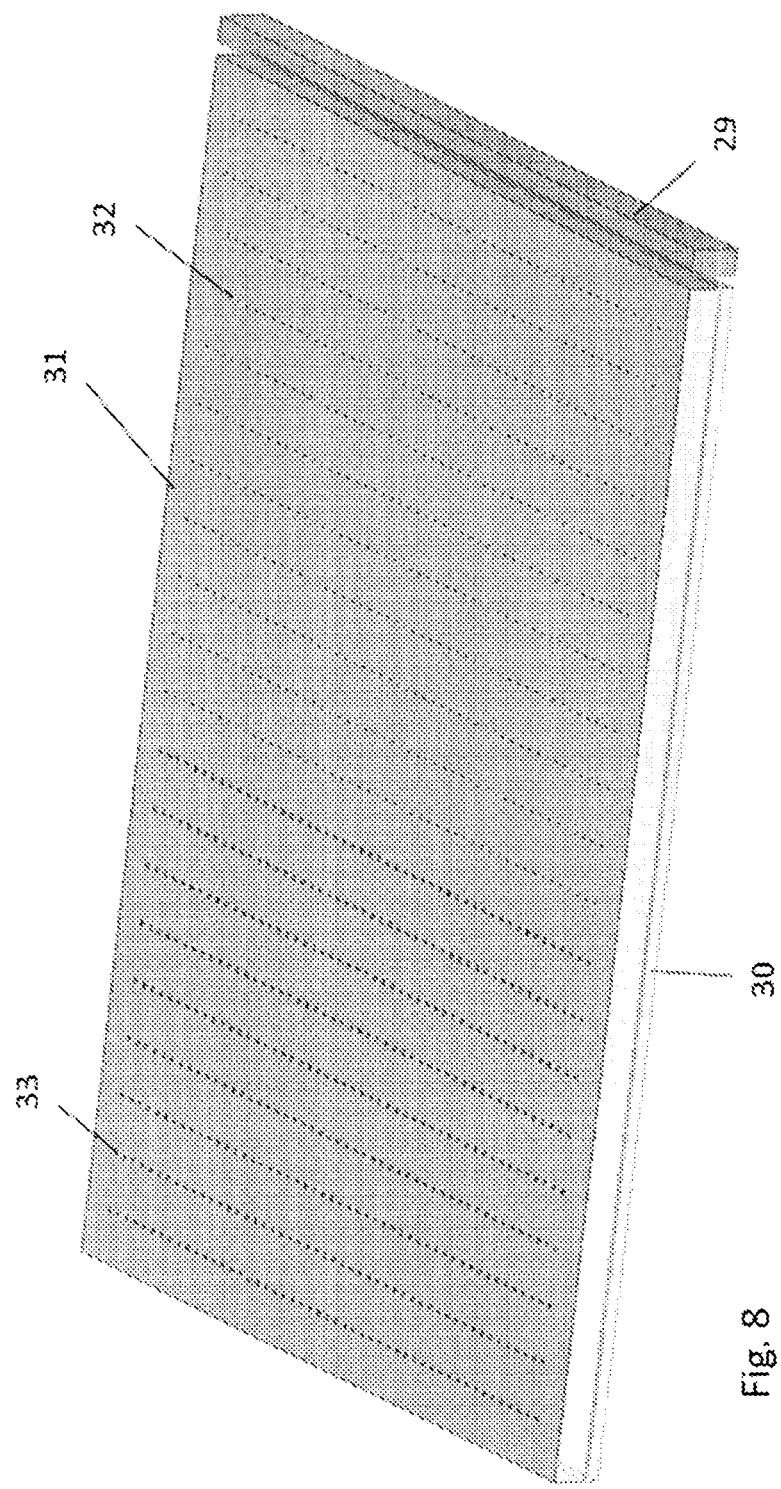
FIG. 8 is a detail of the diffusor panel, axonometric view.

FIG. 8 schematically shows the components of said diffusor panel 68.

FIG. 8 shows said LED strip 29, a reflecting panel 30 and a transparent optical panel 31. Said optical panel 31 is provided with a plurality of holes 32, 33 obtained through laser. Said holes are distributed according to modes and dimensions suitable for ensuring a uniform diffusion of the light between the point closer to and farther from said LED strip 29. As can be observed in the Figure, the holes 32 placed on the right of the panel, nearer to the LED strip 29, are of smaller dimensions with respect to the holes 13 placed on the left of the panel, farther form said LED strip 29.

Said LED strip 29 emits light rays in a way that is parallel with respect to optical panel 11 and reflecting panel 30.

Said reflecting panel 30, placed behind said optical panel 31, directs the light beam, emitted co-planarly with respect to the panel itself, orienting the light beam in an orthogonal way with respect to the emission axis of the light by said LED strip 29.

In a first, simpler embodiment, said LED strip 29 comprises LEDs emitting white light, or anyway LEDs emitting light of just one color. If LEDs emit white radiations (wavelength 400-700 nm), said gantry 3 emits a diffuse and pleasant light which can contribute to patient's relaxation. When said radiographic apparatus is electrically supplied, said housing 60 lights up.

In an embodiment, said LEDs are dimmerable, i.e. the light intensity emitted can vary correspondingly to commands emitted by a (not shown) control unit of said radiographic apparatus 1. For example, the light might be more intense when the set-up of the apparatus 1 is prepared and the patient is accommodated on said gurney 6, and become paler when X-ray emission occurs, always with the aim of maintain patients in a relaxed state.

In a second embodiment, said LED strip comprises LEDs emitting light of different wavelengths, preferably red, yellow and green light. Traditionally, red light indicates a state of stopped apparatus or danger, yellow light indicates that the apparatus is emitting X-rays, while green light can be associated with a condition wherein the apparatus is ready for use. This is a simple and intuitive color coding, which allows to communicate to human users the status of the radiographic apparatus 1.

The control unit of the radiographic apparatus 1 provides to the automatic emission the pre-set color in correspondence of the status of the apparatus 1.

In an embodiment, only the carter 6 oriented towards said patient table 2 is provided with the possibility of emitting light.

In an alternative embodiment, even on the side of the gantry 3 which is opposed to patient table 2 there is provided a housing emitting light.

To the skilled man it is apparent that the same kind of lighting housing can be placed in any position of the apparatus 1, e.g. on one or two sides of said gantry 3.

Finally, in an embodiment, the radiographic apparatus 1 emits at the same time a light signal in one of the above-described forms and an acoustic signal during the emission of X-rays.

According to a further feature, the gantry may be divided in two or more translucent zones each one being associated to an independent light source as indicated by the exemplary embodiment of FIGS. 7 and 8.

Here, without any limitation, the frontal wall of the gantry made of translucent material is formed by four sectors 61, 62, 63, 64 which are separated by radial separation lines preferably extending over the entire thickness of the frontal wall and being of material not transparent to light so to isolate each of the sectors 61 to 64 from the adjacent ones.

Similar construction can be provided for the diffusor panel 68. In fact, differently from the embodiment of FIG. 7, in which the four sectors are commonly associated to only one common diffusor panel 68 having the construction of FIG. 8, according to the further embodiment each sector can be associated to a separate diffusor panel each one having the construction of FIG. 8 and thus a dedicated light source, each one transmitting light respectively only to one of the four sectors, so that by providing different light sources or differently driving the light sources of each separate diffusor panel, each sector 61, 62, 63, 64 can be lighted up separately and independently from the other and with a different light effect.

The present example shows four sectors 61 to 64 dividing the front panel 68 surrounding the hole 107 in four quadrants. Of course, this division is not limiting and the different sectors may be not equal in dimensions one to the other.

Furthermore, according to a further feature two, three or more different sectors may be provided forming the upper half of the transparent front wall 60.

Each light source of each radiation panel can be driven a different and dedicated driver unit, which is controlled by a central control unit. This control unit is linked either by a control software executed by the control unit on the base of the status signals which may be associated to functional status of the apparatus and/or of the radiation source to the radiation source or to other status sensors provided in the apparatus.

According to a further feature, the control unit may be also linked for example by means of a radio or other Wi-Fi communication system to a light source at the door controlling the entrance to the room in which the apparatus is installed and/or to other visual and/or acoustic signaling devices.

LIST OF REFERENCE NUMBERS

1 radiographic apparatus
2 table
3 gantry
4 device for immobilizing patient's head
5 screen
6 gurney
7 base
8 lock/unlock system
9 handle
10 moto-reducer
11 drive belt
12 pulley
13 pulley
14 shaft
15 plate
16 spring
17 female disk
18 male disk
19 pin
20 fixed bracket
21 mobile bracket
22 spring pin
23 dis-insertion hole
24 eccentric pin
25 proximity sensor
26 insertion hole
29 LED strip
30 reflecting panel
31 optical panel
32 hole
33 hole
60 front translucent housing
61, 62, 63, 64 sectors of the translucent housing
65 back translucent housing
68 diffusor panel
107 gantry hole

The invention claimed is:

1. An imaging apparatus comprising: a patient table configured to support a lying patient, the patient table comprising a gurney and a base, the gurney being configured to slide along a longitudinal direction between two extreme positions in relation to the base; an electrically supplied moto-reducer-controlled by a control unit, configured to slide the patient table along at least one spatial axis; and a lock/unlock system of a sliding of the patient table, wherein the lock/unlock system of the sliding is a mechanical system independent from the electrical supply, manually controlled by a handle adapted to be actuated by a human operator, wherein the imaging apparatus is adapted for positioning the lying patient in a radiographic apparatus and is provided in combination with the radiographic apparatus, wherein the radiographic apparatus is a cone-beam computerized tomography (CBCT) scanner, a spiral computerized tomography scanner, a Magnetic Resonance Imaging (MRI) scanner, or a Position Emission Tomography (PET) scanner, wherein the lock/unlock system comprises a first and a second opposing element, the first and the second opposing elements being respectively mounted on a first and a second shaft independently rotatable with respect to each other, at least one of the first and the second opposing elements being axially movable in a direction of insertion and disconnection of the first and the second opposing elements in an axial direction of the first and the second opposing elements, wherein the lock/unlock system is provided with a first fixed bracket and a second mobile bracket, wherein, at a first end opposed to a second end grabbed by the human operator, the handle is provided with a spring pin which engages alternatively: in an insertion hole obtained in the first fixed bracket, blocking the lock/unlock system in a position wherein a motion of the moto-reducer is transmitted; and in a dis-insertion hole obtained in the first fixed bracket blocking the lock/unlock system in a position wherein the motion of the moto-reducer is idle, wherein the lock/unlock system comprises a proximity sensor recognizing an axial position of the handle, and wherein, when the spring pin is inserted in the insertion hole, the sensor is active and communicates to the control unit of the radiographic apparatus causing the gurney to be moved automatically, and wherein, when the handle is extracted from the insertion hole, the sensor is inactive, signaling to the control unit that the moto-reducer is idle.

2. The imaging apparatus according to claim 1, wherein handle is adapted to be actuated between two extreme positions: a first position that is a block position, in which the handle activates an insertion connection between a moto-reducer actuated by the control unit of the radiographic apparatus and the gurney for transmitting an actuating motion of the moto-reducer to the gurney; and a second position that is an unblock position, in which the handle brings the insertion connection in a dis-insertion position between the moto-reducer actuated by the control unit of the radiographic apparatus and the gurney, and in which the moto-reducer is idle.

3. The imaging apparatus according to claim 2, wherein X-ray emission is blocked when the lock/unlock system is in the dis-insertion position.

4. The imaging apparatus according to claim 1,
wherein the lock/unlock system comprises a drive belt actuated by the moto-reducer moving a pulley mounted on the first shaft,
wherein, on the first shaft, a plate is fixed that rotates integrally to the shaft; on the first shaft, and
wherein the first opposing element is a first disk integral to the first shaft, which represents a female element of mechanical insertion, and the second opposing element is a second disk, which represents a male element of the mechanical insertion and is disposed to slide in relation to the first shaft.

5. The imaging apparatus according to claim 4,
wherein the first disk comprises a plurality of springs working in compression on the first disk, the first disk being free to axially slide with respect to the first shaft when the plurality of springs are compressed, and
wherein the second disk comprises a plurality of pins, the first disk comprising a plurality of holes on which the plurality of pins engage.

6. The imaging apparatus according to claim 1,
wherein the handle is adapted to be actuated by the human operator in patient positioning to position the gurney before acquiring a radiographic image, and
wherein the patient table is provided in combination with a gantry having a housing transparent to light radiation for at least part of a surface extension thereof,
further comprising a second control unit controlling the radiographic apparatus,
wherein a light source of monochromatic or polychromatic light radiation is associated to the housing or a part thereof, and the second control unit is configured so as to cause one or more status sensors, when the radiographic apparatus is electrically supplied, or another predetermined status condition is detected, the light source to be illuminated and the housing to light up in translucent parts thereof signaling the predetermined status condition.

7. The imaging apparatus according to claim 6,
wherein the light source of monochromatic or polychromatic light radiation lighting the housing is a LED strip emitting white light of a wavelength in a range of 400-700 nm, or wherein the light source lighting the housing is a LED strip emits light of different colors,
wherein the LED strip is configured to be dimmed or pulsed in a sequence under control of the second control unit, and
wherein emission of a specific color or in a predetermined sequence of pulsing indicates one or more status conditions comprising a situation of stopped radiographic apparatus, a situation of danger, a status condition of the lock/unlock system, and or an indication of a radiation source being active or inactive.

8. The imaging apparatus according to claim 7, wherein:
emission of yellow light indicates that the radiographic apparatus is emitting X-rays for a radiographic acquisition;
emission of green light indicates that the radiographic apparatus is ready for the radiographic acquisition,
emission of red light indicates a generic condition of danger and a need of activating the lock/unlock system to set free the gurney.

9. The imaging apparatus according to claim 7, wherein the housing is provided with two or more optically separated transparent zones each associated to a separate light source, each separate light source being driven independently from another light sources in relation to a light effect generated as a color, an intensity, or the sequence of pulsing of the light source.

* * * * *